United States Patent [19]

Mennen et al.

[11] Patent Number: 4,562,043

[45] Date of Patent: Dec. 31, 1985

[54] SELF-CONTAINED SWAB CARTRIDGE APPARATUS FOR DETECTING OCCULT BLOOD

[76] Inventors: Frederick C. Mennen, 506 Clay St., LaPorte, Ind. 46350; Ronald Freake, P.O. Box 171, Tulsa Rosa, N. Mex. 88352

[21] Appl. No.: 530,649

[22] Filed: Sep. 9, 1983

[51] Int. Cl.$^4$ .................... G01N 21/78; G01N 33/72; C12M 1/30

[52] U.S. Cl. .................... 422/56; 128/638; 128/749; 422/58; 422/61; 435/294; 435/296; 435/810; 436/66

[58] Field of Search ............. 128/638, 749, 756, 759; 422/61, 58, 102, 56; 435/294, 295, 296, 810, 292, 28; 436/66 X

[56] References Cited

U.S. PATENT DOCUMENTS

| | | | |
|---|---|---|---|
| 3,446,596 | 5/1969 | Salivar et al. | 435/296 X |
| 4,018,653 | 4/1977 | Mennen | 435/296 X |
| 4,071,317 | 1/1978 | Lam | 436/66 X |
| 4,148,611 | 4/1979 | Nand et al. | 436/66 |
| 4,199,550 | 4/1980 | Wielinger et al. | 436/66 X |
| 4,273,741 | 6/1981 | Levine | 128/759 X |
| 4,340,670 | 7/1982 | Mennen | 422/61 X |
| 4,355,113 | 10/1982 | Mennen | 435/295 |
| 4,447,542 | 5/1984 | Gantzer | 435/28 X |
| 4,521,520 | 6/1985 | Jacke | 422/56 X |

OTHER PUBLICATIONS

Ostrow et al., Digestive Diseases, vol. 18, No. 11, pp. 930–940, 1973.

*Primary Examiner*—Arnold Turk
*Assistant Examiner*—Robert J. Hill, Jr.
*Attorney, Agent, or Firm*—A. A. Saffitz

[57] ABSTRACT

A tubular test device for testing occult blood in fecal matter using hydrogen peroxide in an ampoule and 3,3′,5,5′-tetramethylbenzidine as the chromogen dissolved in chloroform to impregnate a cellulosic pledget which, when dried, is substantially colorless and is introduced adjacent a sampling swab into the device to lie adjacent the ampoule containing dilute hydrogen peroxide and a wetting agent. A special conditioning precoating for the pledget before impregnation with liquid chromogen in chloroform is provided consisting of hydroxyethylcellulose dissolved in an aqueous nonvolatile acid buffer such as citric acid and sodium citrate to maintain a pH of 5–7, and then dried. The swab takes a sample of fecal matter. A cap is placed over the swab. The ampoule is broken. If fecal blood is present the hydrogen peroxide passes to the pledget aided by capillary action to create an intense green coloration in the cap very rapidly if the pledget is in the cap above the sampling swab and very slowly if the pledget is below the sampling swab. The color developed for a positive test is exceptionally long-lasting in the cap portion when 6-methoxyquinoline is added to the chromogen in chloroform in making the pledget. In contrast to the guaiac test which fades, the color with the enhancer has not faded after 8 months at room temperature, yet the color developed in the pledget in the cap in about 1 to 2 second.

7 Claims, 12 Drawing Figures

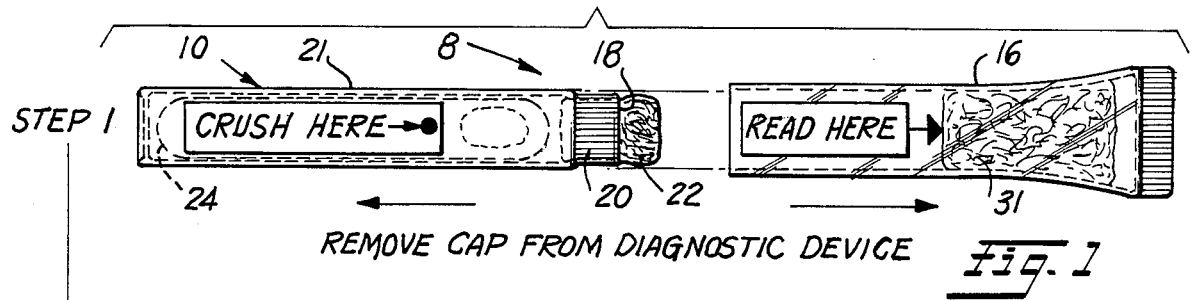
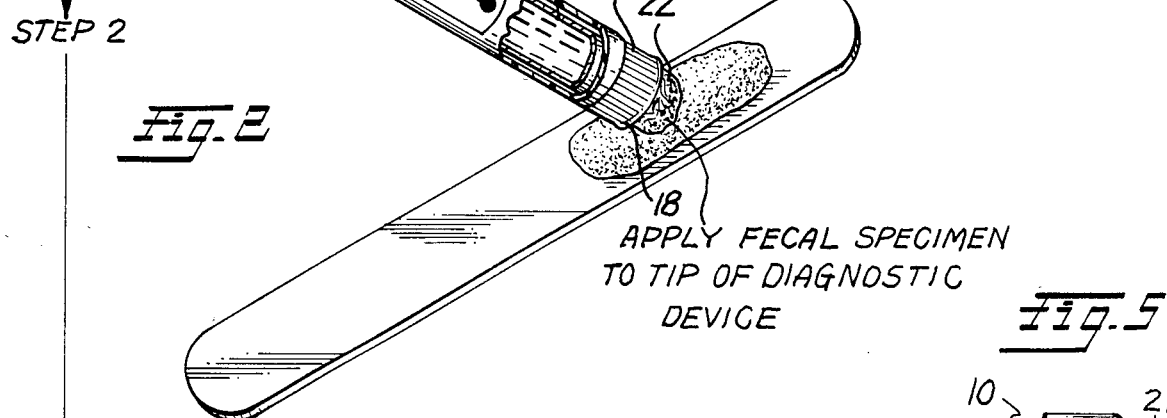
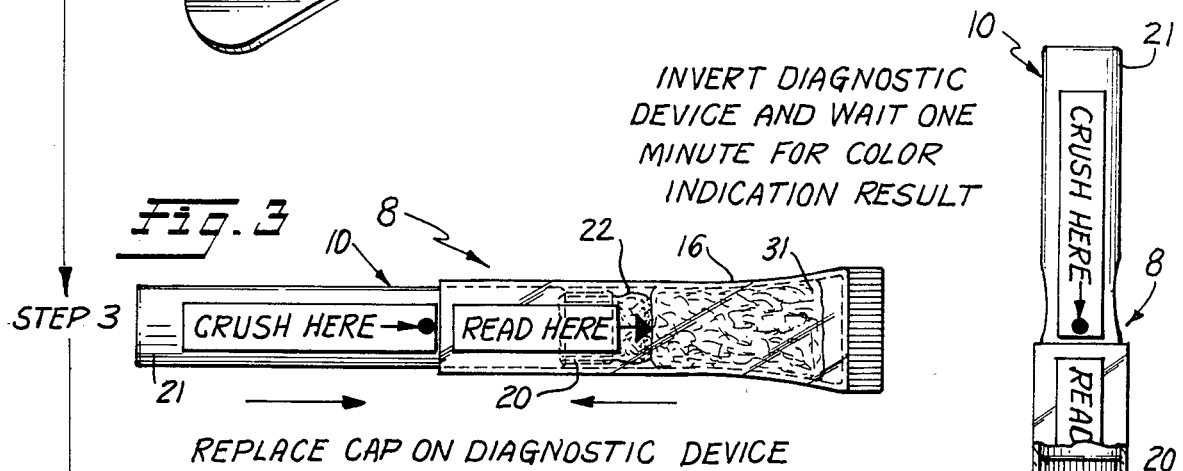
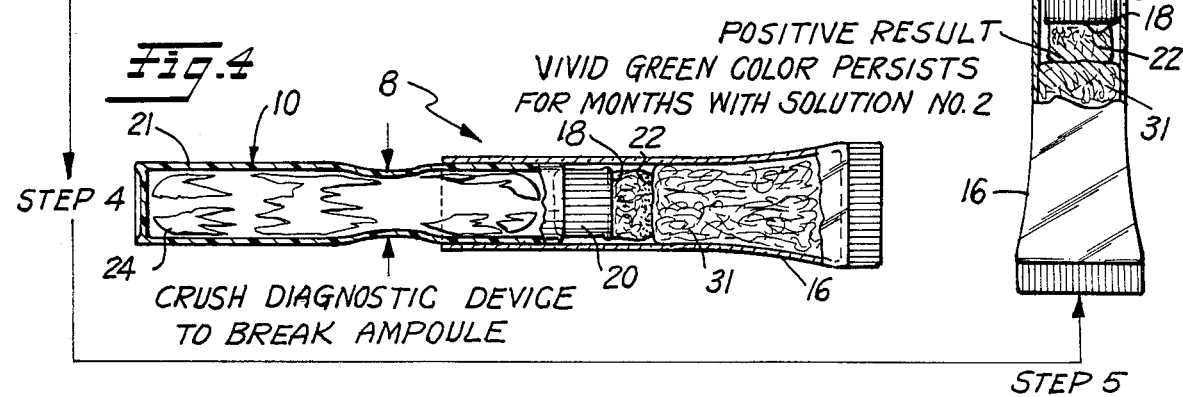

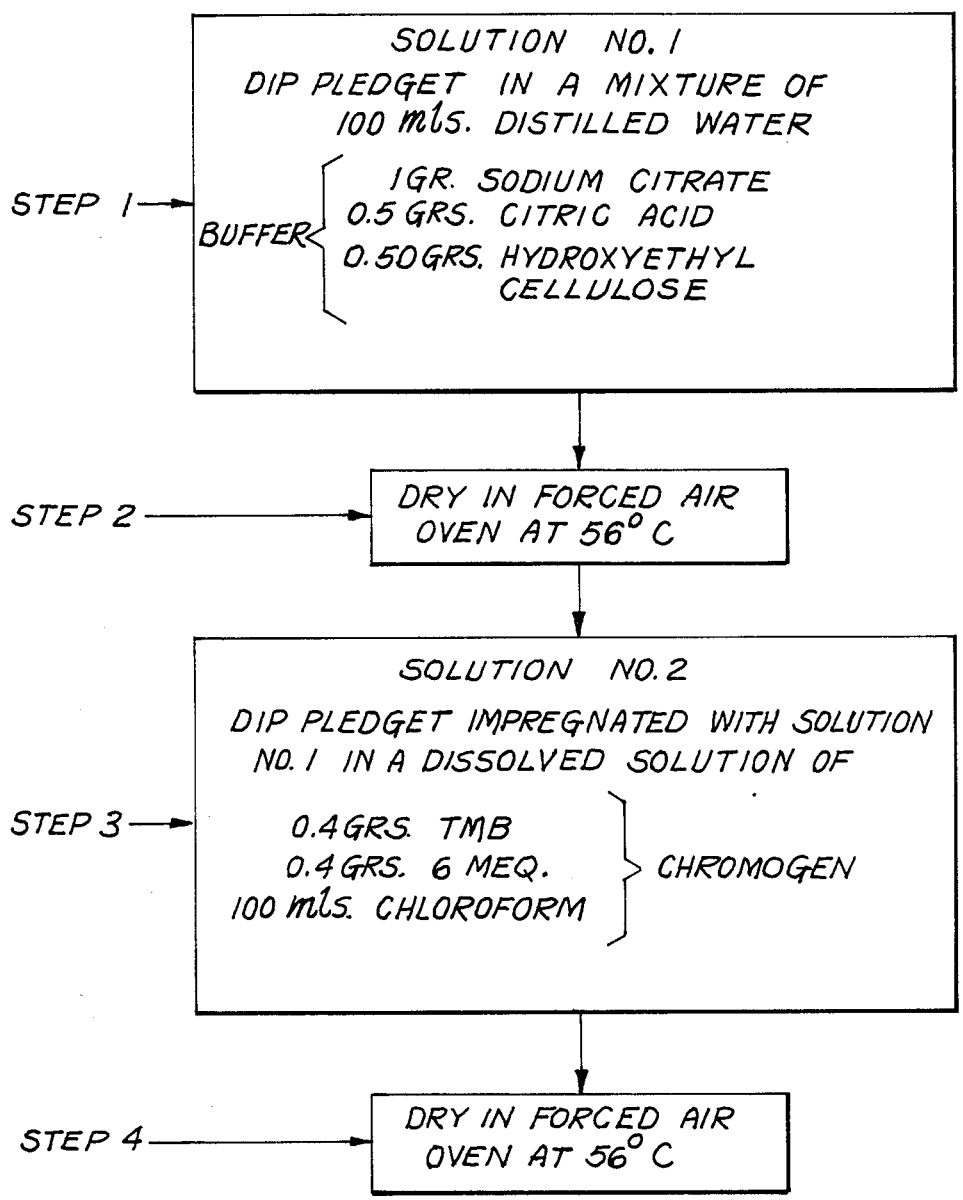
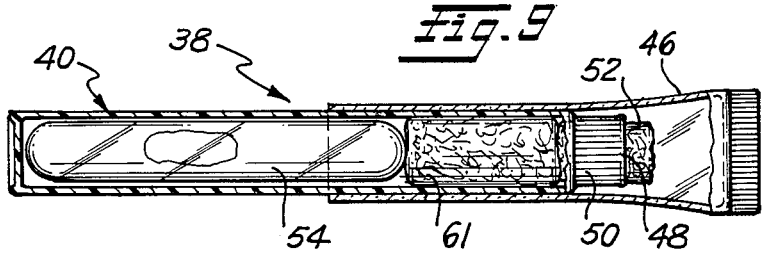

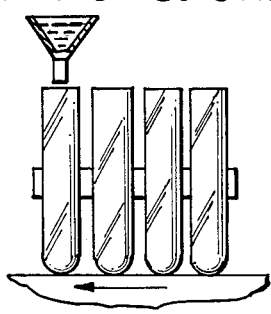

SELF-CONTAINED SWAB CARTRIDGE APPARATUS FOR DETECTING OCCULT BLOOD

BACKGROUND OF THE INVENTION

1. Field of the Invention

This invention is in the field of apparatus and methods of testing utilizing over-the-counter testing kits for self-detection similar in construction to the devices described in Frederick C. Mennon, U.S. Pat. No. 4,340,670 granted July 20, 1982 and U.S. Pat. No. 4,355,113 granted Oct. 19, 1982.

This invention, more specifically, is in the field of diagnostic testing of occult blood based upon the occurrence of the peroxidase enzyme which is used with 3,3',5,5'-tetramethylbenzidine, hereinafter called TMB, as a sensitive non-toxic substitute for benzidine or o-tolidine in an apparatus of the type in U.S. Pat. Nos. 4,340,670 and 4,355,113 comprising an ampoule of hydrogen peroxide in a tube, a pledget impregnated with this sensitive substance and pre-coated with a special water-soluble film-forming hydroxyethylcellulose to provide a test in the cap of the apparatus instead of on the microscope slide which is ordinarily used in the hydrogen peroxide testing method.

2. Description of the Prior Art a. BENZIDINE HYDROGEN PEROXIDE TEST

The hydrogen peroxide testing method which is ordinarily used in described in the article by Holland, Saunders, Rose and Walpole, Tetrahedron, Vol. 30, Pages 3299 to 3302, Pergamon Press, 1972. This article gives the history of the benzidine hydrogen peroxide test going all the way back to 1904 in an article by Adler, et al in Zeitschrift fur Physiologica Chimie, Vol. 41, Pages 59–66 (1904). One of the authors of this Tetrahedron article, Saunders, is a well-known expert in the Peroxidase enzyme system and is the author of the most widely used text "Peroxidase", published by Butterworths, London, 1964.

b. TOXICITY OF BENZIDINE COMPARED WITH TMB

ACS Monograph, 173, Chemical Carcinogens, Charles E. Searle, Editor, American Chemical Society, Washington, D.C., 1976, at Page 481 in the chapter Chemical Carcinogens as Laboratory Hazards, prepared by the Editor of the Monograph, evaluates the test for fecal occult blood as carried out in Great Britain as "the most important encounter with carcinogenic chemicals in hospital and other laboratories." Extensive epidemiological tests which were carried out were the result of the attention paid by the British Government to occupational bladder cancer among British factory workers immediately after World War II. The most complete evidence of the dangers of benzidine and o-tolidine come from these British studies.

The basic clinical test is the application of TMB in acetic acid on a microscope slide which is that described in Tetrahedron by Holland, Saunders, Rose and Walpole, and this test is accepted by most hospital pathology departments throughout the world. The recommendation is made in Tetrahedron to substitute non-carcinogenic TMB for benzidine or o-tolidine in the aqueous acetic acid system for the following two reasons:

1. The sensitivity of TMB to the entire color spectrum in the peroxidase blood test is four times greater than either benzidine or o-tolidine in the water system to present an obvious advantage of sensitivity.

2. The toxicity study by subcutaneous injection of benzidine and o-tolidine and TMB into rats showed substantially no carcinogenic activities for TMB whereas a high incidence of tumors were found with benzidine and o-tolidine.

c. NON-USE OF TMB

The inventors believe that the reason that the TMB occult blood test is more widely referred to in literature of clinical analyses and pathology rather than the patent and trade literature is based in the cancer studies in England and in particular the great interest in avoiding carcinogenic benzidine and o-tolidine.

In 1976 Monograph 173 stated:

"3,3',5,5'-Tetramethylbenzidine, now being advertised as a sensitive substitute for benzidine in the detection of blood, has produced no tumors specifically attributable to it when injected subcutaneously into rats in doses greater than those in which benzidine and o-tolidine cause a high yield of neoplasms. In view of its close relationship to these carcinogens, however, more comprehensive biological tests seem desirable before it is accepted as safe for widespread laboratory use."

d. CHROMOGEN SENSITIVITIES COMPARED

At Page 483 of ACS Monograph, 173, the requirements for the test and sensitivity are mentioned. The detection of gastrointestinal bleeding is of major importance. The blood may be present as intact erythrocytes or as hemoglobin. A suitable test should be such that blood loss of more than 4.5 ml/day can be detected.

"The order of sensitivity of the chromogens used has been o-tolidine > benzidine > phenolphthalein > guaiac. Owing to the carcinogenicity of benzidine and o-tolidine, the choice now lies betwen phenolphthalein, guaiac, or one of the more recent methods." However, the color fades.

e. GUAIAC METHOD AND FADING

The guaiac method which is mentioned for the hospital test in the United States is the method of Hoerr et al: "One such method marketed in the United States utilizes the method of Hoerr et al., in which the specimen of urine or feces under test is placed on a piece of guaiac-impregnated electrophoresis paper. A drop or two of hydrogen peroxide is added; the extent and rapidity of appearance of a blue ring indicates the quantity of blood present."

From the above discussion in Tetrahedron and in the ACS Monograph, it was clear that a selection of TMB for its non-toxic characteristics was not made because of the expected risks in the selection of TMB. No device exists to prevent hospital personnel and laboratory workers from coming into contact with toxic reagents. No useful purpose is gained in providing a blood test by merely substituting TMB for the dangerous benzidine or o-tolidine if there is no likelihood of the test being adopted.

In each of Mennen, U.S. Pat. Nos. 4,355,113 and 4,340,670, a device for diagnosis is disclosed in which the color which is created at the tip becomes progressively darker when the test is positive for gonorrhea. The test color must be read within 90 seconds. If no color develops the test is negative, yet in 5 minutes oxidation creates color. The chromogen is soluble in water in both Mennen U.S. Pat. Nos. 4,355,113, and 4,340,670.

f. DISTINCTIONS OVER MENNEN U.S. PAT. NOS. 4,355,113 AND 4,340,670

The present inventors, in trying to modify the technology of this Mennen Patent to provide a safe device which would eliminate all possibility of laboratory workers or hospital personnel from coming into contact with the chromogen reagent was not obvious or apparent. The chromogen reagent, TMB, is not water-soluble. Some means had to be provided to make it transportable from the pledget in order to take part in a color change when there was an indication of occult blood in the sample of fecal matter. It was surprising to find that the color could be created in the cap of the device if the pledget is precoated with hydroxyethylcellulose and the pledget is placed in the cap in the form of an absorbent plug. It was further surprising to find that the absorbent plug placed in the cap with a positive color and the cap removed may be separately corked or closed and can be left at room temperature for as long as 8 months. This is an unexpected result which frees the doctor from the risk of interruption following the initiation of a testing procedure.

The concept of apparatus which provides a reactive reagent in a frangible container is known in Salivar, U.S. Pat. No. 3,446,596. The reactive unstable material in the present invention is the TMB which is not in the glass ampoule but in the pledget itself.

However it is essential to transport the water insoluble chromogen which must first be deposited and impregnated in the cellulosic pledget material in substantially colorless form and then released by the use of hydrogen peroxide containing liquid from the ampoule.

It was unexpected to discover that the combination of a water-soluble binder, hydroxyethylcellulose which pre-treats the pledget permits the chromogen to be effectively and totally released by the liquid hydrogen peroxide if it contains as a wetting agent, a small amount of *sodium dodecyl sulphate to assure the complete solubilization of the hydroxyethylcellulose.

*sodium decyl sulphate may be used instead g. 6-METHOXYQUINOLINE WITH BENZIDINE AND TMB

Adams, et al, U.S. Pat. No. 3,290,117, granted Dec. 6, 1967 shows quinine, quinoline derivatives, including 6-methoxy-quinoline (6-MEQ) and other compounds for enhancing the color development of chromogens of the benzidine series.

White U.S. Pat. Nos. 4,251,222, 4,251,223, and 4,278,349 compare the 6-methoxyquinoline and o-tolidine in the wet hydrogen peroxide testing method. The earlier White patents concluded that the 6-methoxyquinoline is not as good a sensitizer as the specific sensitizers which were proposed and claimed in each of these patents.

Each of the White patents compared fresh and aged samples in a table 1 which summarized testing of a fresh solution and a sample stored at 60° C. for one week. The purpose of this one week storage is to break down organic matter in the sample. In the absence of 6 MEQ the requirement of the o-tolidine goes from 0.332 mg. per deciliter for a fresh sample to greater than 0.805 mg. per deciliter for an aged sample. This shows an increase of almost three times.

With 6-methoxyquinoline the improvement in o-tolidine requirement is not as great as with the sensitizer claimed in each White patent. White mentions that TMB would give a similar result as o-tolidine.

h. SURPRISING RESULT OF COMBINING TMB AND 6 MEQ

It was unexpected to discover that the developed color for a positive test using TMB by the method of the present invention utilizing the free TMB base in chloroform solution to impregnate a special pledget precoated with hydroxyethylcellulose would provide a long-lasting color and there would be no slowing down of the color development in from 20 to 30 seconds after the ampoule of hydrogen peroxide was broken simply by adding an equal amount of 6 MEQ to the TMB used for impregnating the solution. This is the first instance which the inventors had ever encountered of color development achieved at the start of the test remaining unchanged over a long period of time, up to about 8 months. Its discovery was surprising.

OBJECTS OF THE INVENTION

It is an object of the invention to provide a practical device to improve testing over the aforesaid White patents by the ability to use a non-toxic chromogen rather than a toxic chromogen in an apparatus which makes the handling of the non-toxic chromogen much safer than in the normal testing methods using a paper strip or in the testing on a microscope slide without any time limitation on color development protocol.

A further object of the invention is to provide a cellulosic pledget for impregnating a chromogen in the form of TMB applied to a precoated form of the cellulosic pledget in which the precoating consists essentially of hydroxyethylcellulose and a water soluble salt of an acid with a non-volatile acid providing a buffer whereby the TMB chromogen is conditioned for transport in water to form an aqueous solution for testing blood in fecal matter or in urine and wherein the solution formed passes through the sample for collection in a cap of the device.

A further object of the invention is to provide a long-lasting solution in which the chromogen TMB is combined with an equal amount of 6 MEQ.

Other and further objects will be seen from the following more detailed description, examples, and drawings.

SUMMARY OF THE INVENTION

The technology of Mennen U.S. Pat. Nos. 4,355,113 and 4,340,670 is applied to testing occult blood in fecal matter using hydrogen peroxide and 3,3',5,5'-tetramethylbenzidine, TMB, as chromogen. The TMB is dissolved in chloroform to impregnate a cellulosic pledget which must be pre-coated with hydroxyethylcellulose and a buffer. Thus the pledget is doubly coated and is substantially colorless. The pre-coating of the pledget is essential to provide the chromogen in a form in which it can be easily transported by the liquid hydrogen peroxide in the form of a dilute 1–3% aqueous solution to react with the occult blood in the sample of fecal matter. The device is similar to the construction of the aforesaid Mennen U.S. patents in that the pledget which is doubly coated may be placed under the sampling swab or it may be placed over the sampling swab in the cap of the device. The sampling swab serves to carry a small sample of fecal matter containing occult blood. A frangible ampoule containing dilute hydrogen peroxide and a wetting agent, preferably sodium decyl sulphate is placed at the bottom of the tube below the swab. The tube is flexible to permit the frangible ampoule to be broken by placement between the finger and thumb and pressing. Liquid hydrogen peroxide passes through the sample and also passes through the pledget which is double-coated.

If the pledget is placed in the cap above the swab, color develops within 1 to 2 seconds, e.g. immediately. If the pledget is placed below the swab and next to the ampoule, then the color develops very slowly, from 2 to 5 minutes. The color development in this case is not reproducible in time, that is to say, within a given time one can not be assured that the same intensity of color will develop for the same sample and for this reason the color development is preferably with placement of the pledget above the swab and in the cap portion.

The construction of the pledget, which in the preferred form comprises a thin web of cellulosic material available under the Trademark WEBRIL (⅛ inch thickness or 1/64 inch thickness) is physically adapted by its high absorbency to be impregnated with a dilute solution of hydroxyethylcellulose in a wetting agent such as *sodium decyl sulfate together with a buffer such as citric acid and sodium citrate. The buffer consists of a non-volatile acid with a water soluble salt of the acid which will give a pH in the range of pH5–pH7. A non-volatile hydroxy acid which is polybasic such as citric acid or tartaric acid is preferred. Other polybasic acids may be used which are non-volatile. Organic acids are preferred over inorganic acids. Acids such as lactic, malic, citraconic acids may be used. The water-soluble salt may be a potassium salt or a sodium salt. Other water-soluble salts may be used but are not preferred for reasons of economy and availability.

*sodium dodecyl sulphate may be used instead

The function of the hydroxyethylcellulose is to permit the use of the chromogen in the form of a free base. If hydroxyethylcellulose is not present the hydrogen peroxide in liquid form used with only the buffer in the pledget serves to provide a non-reactive mixture which does not produce the desired rapid color development. If the buffer is deleted, then the immediate color formation is not observed, e.g. within 1 to 2 seconds, and the test can not be made uniform and reproducible. It appears that the chemical reaction leading to color developments because of the presence of the active hemin portion of the molecules of blood with hydrogen peroxide and peroxidase requires the solubilization of the TMB in the form of a salt. Here the salt is the salt of citric acid if citric acid is the buffer, as it is in the preferred embodiment. In the presence of sodium citrate which adjusts the buffer pH to the optimum pH for rapid color development and in the presence of the hydroxyethylcellulose which provides the medium for salt formation there is achieved a rapidity of color development which had never heretofore been observed for examples of impregnation of the free base itself in an inert cellulosic carrier.

Surprisingly, the addition of 6 MEQ, preferably an equal amount of 6 MEQ, enhances the color stability by providing a longlasting color. It appears in some instances the color is slightly deeper but in all cases the color will last longer than 48 hours. There has been no appreciable fading after 2 weeks, or 2 months, or after 8 months and present results and observations indicate that the color may last for as long as 2 years. The color may appear in the liquid by squeezing out the liquid in the cap and in this preferred form of the device it is possible to insert paper strips which can pick up the color and become part of the doctor's records. In the preferred form, the cap contains a pledget in the shape of a cotton plug, the pledget being doubly coated, and after sampling the fecal matter in the swab, the cap is placed over the pledget and the sample to close the device. The ampoule is broken and the liquid hydrogen peroxide and sodium decyl sulfate pass by capillary action through the swab to reach the pledget and to create an intense green coloration in the pledget which is located in the cap in the preferred form with TMB as chromogen and 6 MEQ added to prolong the color, the color forms in 1 to 2 seconds and is exceptionally long-lasting in the cap portion. The hydroxyethylcellulose which is dissolved in water containing sodium decyl sulfate serves as a special conditioning pre-coating for the pledget which is compatible with the essential non-volatile organic acid needed to form the acid salt of the chromogen in the preferred case, the citrate salt. The preferred non-volatile acid is used together with a water-soluble salt of the acid such as the sodium or potassium salt and the combination forms a buffer which assures a condition for rapid color development of TMB into the intense green color resulting from the presence of occult blood. The aqueous buffer which is regenerated by the breaking of the ampoule and release of liquid dilute hydrogen peroxide provides a pH of the aqueous medium for color development between pH 5 and pH 7. The wetting agent, sodium decyl sulfate which is present in the hydrogen peroxide ampoule, performs the function of completely dissolving the hydroxyethylcellulose coating which contains the buffer. The hydroxethylcellulose binder is soluble in an aqueous solution of sodium decyl sulfate to the extent of more than 98.5% at a pH of 6–8 at 25° C. The hydroxyethylcellulose which is employed for the pre-coating provides a relatively low viscosity in the solution which is used to impregnate the pledget in the pre-coating operation and the same low viscosity is observed when the liquid from the hydrogen peroxide transports the chromogen and sample into the cap.

BRIEF DESCRIPTION OF THE DRAWINGS

FIG. 1 is an exploded side elevational view of a preferred form of the diagnostic device of the present invention in which the chromogen-pledget is in the cap;

FIG. 2 is a view illustrating the procedure for obtaining a fecal specimen on the exposed tip of the cotton plug portion of the diagnostic device with the cap of the device removed;

FIG. 3 is an assembled side elevation of the diagnostic device of FIG. 1 with the cap replaced to assure that the fecal material touches the chromogen-pledget;

FIG. 4 is a longitudinal sectional view of the reassembled diagnostic device of FIG. 3, partly in elevation, showing the next step in which the ampoule is crushed in order to release the diagnostic hydrogen peroxide reagent solution contained therein;

FIG. 5 is a vertical elevational view, partly in section, after the ampoule is crushed and the device is inverted showing the contact of the liquid hydrogen peroxide passing through the cotton plug into the chromogen-pledget to thereby provide the result of the diagnostic test utilizing the preferred embodiment with the chromogen-pledget in the cap;

FIG. 6 is a schematic series of steps showing the method of preparing the chromogen-pledget by precoating in solution No. 1 and impregnating with organic solvent with solution No. 2;

FIG. 7 is a schematic series of steps showing the method of preparing and filling the ampoule with dilute hydrogen peroxide and sodium decyl sulfate;

FIGS. 8 through 8C are diagrammatic exploded views, on a smaller scale, showing the procedure for assembling the body of the preferred form of the diagnostic device of FIG. 1;

FIG. 9 is a longitudinal sectional view, partly in elevation, similar to FIG. 3, of a less preferred modification of the diagnostic device, wherein the chromogen-pledget is placed in the tube between the ampoule and the cotton sampling swab and wherein the chromogen-pledget in the cap is eliminated.

DESCRIPTION OF THE PREFERRED EMBODIMENTS

The patient for whom the test is designed must be advised of diet restrictions and interfering substances. The patient should adhere to a meat-free high residue diet for at least 2 days prior to and during the testing period to eliminate substances that could possibly interfere with test results. Items to be avoided on this diet are red or rare meat, horseradish, turnips, broccoli, aspirin, and tonics or vitamin preparations which contain greater than 250 mg Vitamin C (ascorbic acid) per day. Items that may be included are small amounts of chicken, tuna, and turkey, fresh and cooked vegetables including lettuce, corn, and spinach, fruits, especially prunes, grapes, plums, and apples, and any kind of bran or bran-containing cereals, popcorn and peanuts in moderate amounts.

Interfering substances. The patient should discontinue or limit the use of oral medications that could interfere with test results such as aspirin, medications containing aspirin or other salicylates, iron preparations, corticosteroids, phenylbutazone, and indomethacin. These should be specifically discontinued for 2 days prior to the test and continuing throughout the test period. The patient should consult his or her physician's advice on the discontinued use of any medication that is deemed to be necessary.

Patients with active bleeding from other conditions that may show up in stool specimens (i.e. menstruation, hemorrhoids, bleeding gums or ulcers) are not suitable test subjects while such bleeding is active.

The name of the patient, patient's address, telephone number, and date of sample should be printed on the patient identification label affixed to the test.

There is shown in FIGS. 1-5 the successive steps of how to use the preferred embodiment of the diagnostic device of the present invention. The specific use distinguishes over both of Mennen prior swab kits disclosed in U.S. Pat. Nos. 4,340,670 and 4,355,113 in that the ampoule does not contain the chromogen or a mere wetting solution for the purpose of dissolving an acid salt in water but instead contains a reagent which chemically provides the peroxidase technology for TMB as the chromogenic indicator and serves as an In Vitro diagnostic test in diagnosing various gastrointestinal disorders while conducting routine physical examinations or in routine testing of in-patients in hospitals and clinics or for screening for colorectal cancer.

The first step which is illustrated in FIG. 1 is the removal of the cap 16 from the diagnostic device 8 so as to expose the projecting tip of the cotton swab 22 which is secured at the indented heat seal area 20 of the open end 18 of the thermoplastic tubular cartridge 10. The thermoplastic tubular cartridge 10 is flexible and is adapted to permit finger and thumb pressure to manipulate and crush an ampoule 24 which is placed below the swab in the tube.

In the preferred commercial embodiment the thermoplastic cartridge is covered with paper to render the tube opaque, the covering 21 being colored yellow for easy identification and bearing the instructions on the body "CRUSH HERE". In the preferred form of FIG. 1 the ampoule 24 is placed directly behind the swab 22.

The filling of the ampoule with hydrogen peroxide and sodium decyl sulfate is shown in FIG. 7 wherein the preparation, filling, and sealing steps are shown in order.

This ampoule 24 holds a volume of about 0.75–1.0 ml. of reagent as 3% liquid hydrogen peroxide (concentration varies from about 2–5%) and about 1% of sodium decyl sulfate (varies from 0.2–1%) in order to transport TMB and the water soluble binder used in impregnating the chromogen-pledget, e.g. hydroxyethylcellulose.

FIG. 8 shows the assembly of the preferred form of the device of the invention which is the device shown in FIG. 1. The assembly steps include the insertion of the ampoule 24 into the tubular body 10, the insertion of the cotton swab 22, the heat sealing in step 3 as shown in FIG. 8B and the final assembly of the chromogen-pledget 31 in the cap 16 as shown in FIG. 8C.

As shown in FIG. 1, in the cap 16 there is provided a printed instruction on the body of the cap which states "READ HERE". This instruction notifies the user that if the color develops it will be read in the cap to indicate that a positive test blood in fecal matter is achieved, that the instruction "READ HERE" will alert the user to expect the color in the cap. The step of sampling requires opening the device by removing the cap 16 in order to apply the sample of fecal matter to the tip of the swab 22 which projects from the open end 18 of the thermoplastic tubular cartridge 10. The illustration of the taking of the sample is shown in FIG. 2 by the provision of the sample material on the flat forward surface portion of the spatula (the wooden tongue depresser is one form which may be used). The cap 16 is is replaced in FIG. 3 and the ampoule is crushed to release its liquid contents, FIG. 4, then inverted to have the liquid pass through the swab 22 to reach the chromogen TMB in the pledget 31 as shown in FIG. 5, within 1-2 seconds. In the less preferred embodiment of FIG. 9, the liquid goes from ampoule 54 through pledget 61 before it reaches the sample on swab 52 and the time for color development of a positive test is from about 2 to 5 minutes.

It is noted that the preferred embodiment shown in FIG. 3 illustrates a cotton chromogen-pledget 31 which is contained within the cap so that when the cap is closed the sampling swab 22 with its sample portion at the projecting tip comes into contact with the cotton plug. This relationship is shown in FIG. 3 and the package insert which is used permits the chromogen-pledget 31 to be viewed through the transparent cap by the user.

In Step 4 the stage of breaking the ampoule is shown in FIG. 4. The legend in step 4 is indicated "CRUSH DIAGNOSTIC DEVICE TO BREAK AMPOULE".

In Step 5, if there is occult blood in the sample, then the color appears in the chromogen-pledget in the form if a vivid green color. The vivid green color, in the presence of 6 MEQ also in the pledget 31, will persist for months. The legend for step 5 which is indicated in the drawings in FIG. 5 is "INVERT DIAGNOSTIC DEVICE AND WAIT ONE MINUTE FOR COLOR INDICATION RESULT:. In the presence of the chromogen only, TMB, in the pledget and without 6 MEQ the color will develop in 1 or 2 seconds but the color will not last for two weeks. With 6 MEQ and TMB the color will develop in 1 or 2 seconds but the color will last 8 months or longer. Thus it is not necessary to wait the full minute. The positive result is the color, vivid green, which appears in the chromogen-pledget which is held in the cap. With 6 MEQ the color will last for months.

SUMMARY OF THE PROCEDURE

The procedure which is printed on the package insert for the device is as follows:

PROCEDURE

1. Remove the clear plastic cap and rub the exposed tip of the cotton plug on the stool sample.
2. Replace the cap making sure the fecal material touches the chromogen pad in the cap.
3. Crush the frangible glass ampoule where indicated on the plastic tube. Invert the tube and allow the fluid to saturate the cotton plug and the chromogen pad. A blue to green color that develops within 3 minutes indicates a positive test.

MANUFACTURE OF THE CHROMOGEN-PLEDGET

A critical aspect of the invention is the preparation of the solution No. 1 for pre-treating the pledget 31 which is needed to prepare the untreated pledget for a water releasing condition for the chromogen, TMB, and the preparation of a solution No. 2 which is an organic solvent solution of the chromogen TMB which is applied after solution No. 1 has been applied to the pledget. These steps of application are shown in FIG. 6 wherein the material for the pledget which is treated to prepare a pledget in the form of a web of cellulose material has been dipped into a special aqueous composition containing sodium citrate—citric acid buffer, hydroxyethylcellulose and, alternatively, a color stabilizing agent, 6-methoxy-quinoline. As shown in FIG. 6 the pledget is dipped, then dried to fix the pretreating solution and then dipped again with the volatile solvent solution which is preferably chloroform, to bring the pure chromogen, TMB in the form of a base into the substantially colorless impregnated form in association with the hydroxyethylcellulose pre-coat containing buffer and color stabilizing agent.

The ampoule 24 contains the hydrogen peroxide solution in a 3% concentration and also contains 1% of sodium decyl sulfate as wetting agent and can not be used with any other reagent. The ampoule 24 can not be used to enclose a solution of the chromogen TMB in chloroform. The chloroform would have to be evaporated in this case. Thereafter the chromogen would have to be reacted with hydrogen peroxide from another source. This variation would require a further aqueous treating solution in another ampoule. This is a difference over Mennen U.S. Pat. Nos. 4,340,670 and 4,355,113.

In contrast to Mennen U.S. Pat. No. 4,355,113 which uses an aqueous salt solution in the ampoule, the hydrogen peroxide reactant containing the 1% solution of sodium decyl sulfate as wetting agent treats the dry pledget which has been impregnated with TMB chromogen after the ampoule is broken as shown in FIG. 4.

In a less preferred embodiment of FIG. 9 with the chromogen-pledget between the ampoule and the sampling swab so that there is no chromogen-pledget member in the cap as in the preferred embodiment, color development is quite slow.

The embodiment of FIG. 9 shows a diagnostic device 38 having a tubular cartridge 40 and a cap 46. The cartridge 40 has an open end through which an ampoule 54 is inserted. An impregnated pledget 61 is then placed between the ampoule 54 and a swab 52. The whole assembly is then heat sealed as shown at 50 and covered by the cap 46. After breaking the ampoule it may take minutes, several minutes up to 5 minutes and the color development when hemoglobin is present in substantial amounts is not reproducibly and uniformly achieved. The appearance of the color in 1 to 2 seconds represents such an enormous advantage over the less preferred embodiment. The preferred embodiment is that illustrated in FIGS. 1–5.

Also, the long life of the positive color test is enhanced by the presence of 6 MEQ in both the preferred and less preferred embodiments and is recommended to serve as a quality control check on the lot number of TMB chromogen which is used to prepare the chromogen pledgets.

EXAMPLE 1

TESTING OF BLOOD SAMPLES TO SHOW EQUIVALENT PERFORMANCE IN THE DETECTION OF FECAL OCCULT BLOOD

A. SENSITIVITY

At U.S. Packaging Corporation, 239 non-fecal laboratory prepared samples spiked with known concentrations of commercially available hemoglobin were tested with OCCULT-ALERT TM and reacted as follows:

| No. of tests | Concentration of hemoglobin | Results |
| --- | --- | --- |
| 20 | 0 mg | All negative |
| 20 | 1 mg | All negative |
| 67 | 4 mg | All positive |
| 66 | 5 mg | All positive |
| 66 | 6 mg | All positive |
| Total 239 | | |

EXPLANATION OF EQUIVALENCY

EXPLANATION: OCCULT-ALERT TM is substantially equivalent in performance to Smith Kline Diagnostics' HEMOCCULT ® product and Helena Laboratories COLOSCREEN, both of which are presently in commercial distribution. The test methodology of OCCULT-ALERT TM is based upon technology currently in the public domain.

EQUIVALENCE: Because of the discrepancies found in the literature and the HEMOCCULT ® package insert with respect to minimum levels of detection, COLOSCREEN was also used in the sensitivity studies.

The discrepancies appear to be relative to the homogeneity of the stool sample. Non-homogeneous sampling which was done in the study by Ostrow et al, "Sensitivity and reproducibility of guaiac, Hematest, and Hemoccult tests for fecal occult blood". (Abstr) Ann. Intern. Med. 76:860, 1972, and referenced in the HEMOCCULT ® package insert yields higher levels of sensitivity (i.e. 10 mg/g) than homogeneous sampling as illustrated in the article by Wells, "Comparison of the sensitivity of two tests for fecal occult blood, Coloscreen and Hemoccult". Am. Assoc. Clin. Chem. 1980 Annual Meeting, Boston, July, 1980, and referenced in the COLOSCREEN package insert (i.e. 4–6 mb/g).

|  | HEMOCCULT ® | COLOSCREEN |
|---|---|---|
| Stated level of detection (Package Inserts) | 10 mg/gm | 4–6 mg/gm |
| Sample Preparation | non-homogeneous | homogeneous |
| Published lower limits of detection (4) | 2–4 mg/gm | 2–4 mg/gm |
| Sample preparation | homogeneous | homogeneous |

To determine equivalency of OCCULT-ALERT ™ to HEMOCCULT ® and COLOSCREEN, a total of 477 tests were performed by the Medical Products Division of U.S. Packaging Corporation, LaPorte, IN.

An additional 286 tests were completed under the supervision of the inventor, Frederick C. Mennen, to provide a total of 763 tests which were performed to demonstrate equivalency.

Equivalency procedures were run with 6 MEQ in dip Solution No. 2. The procedure of FIG. 6 was followed:

| DIP SOLUTION NO. 1 | | DIP SOLUTION NO. 2 | | |
|---|---|---|---|---|
| Natrosol | 0.5 gram | 6 MEQ | 0.4 | gram |
| Citric Acid | 0.5 gram | TMB | 0.4 | gram |
| Na Citrate | 1.0 gram | Chloroform | 100 | ml |
| H$_2$O | 100 ml | | | |
| SOLUTION NO. 3 TO FILL AMPOULE | | | | |
| Hydrogen Peroxide | | 3% Pharmaceutical Grade | | |
| Sodium Decyl Sulphate | | 0.5% chemical in 0.75 ml quantities in crushable glass ampoules | | |

The contrived fecal sample of starch with added human blood to the equivalent of 5 mg. of hemoglobin per gram of total sample was prepared and the equivalency testing determinations were carried out as follows:

The reactivity of the contrived sample was tested against a known testing system, SMITH KLINE AND BECKMAN HEMOCCULT ®. The contrived fecal sample provided a visible color in substantially less than one minute, generally 1–2 seconds of the time after the testing solution was contacted with the sample.

Separate testing was done with a few genuine fecal specimens to which known amounts of hemoglobin were added and it was established that in both systems the color change was camparable in the invention and in the comparison system.

Thus, before the testing was started to compare the diagnostic testing system of the present invention with that of SMITH KLINE AND BECKMAN HEMOCCULT ® and after the initial equivalents were shown for human fecal specimens with both, it was established that the contrived fecal samples would provide a fair comparison with the existing SMITH KLINE AND BECKMAN HEMOCCULT ®.

PHYSICAL PROPORTIONS OF DEVICES

The relative proportions of the diagnostic instruments used in the two testing systems, the occult alert testing system of the present invention and the two Smith, Kline and Beckmann systems each about 2" by 1", SK&B 1 and SK&B 2, the sizes of the respective systems were comparable to each other. To illustrate, referring to FIGS. 1–5, herein, the opaque cylinder had an inner diameter of 5/16 of an inch and a height of 2 inches. It accommodated a frangible glass ampoule which contained either 0.75 ml or 0.1 ml of liquid (combined 3% hydrogen peroxide and 0.5% of sodium decyl sulfate). The crimped portion of the top of the tube which anchored the swab is about 3/16 of an inch and the swab which projects beyond the crimped portion is an additional 3/16 of an inch. The entire length of the tube with swab is about 2 5/16 inches and the anchored portion of the swab from the tip to the rear of the crimped area is about 7/16 of an inch. The cap in the particular prototype which was prepared for the testing demonstration is cylindrical but with a flattened or crimped end 1 15/16 inch long. The cap within the embodiment having the plug placed therein is preferably filled as shown in FIG. 1, the inside diameter of the cap being slightly larger than 5/16 of an inch and the height of the plug being about ¾ of an inch, e.g. slightly less than half of the free inside height of the cap. In this relationship of plug moved to the very end of the cap, the edge of the plug meets the projecting tip of the swab as shown in FIG. 3. With this overlap the entire assembly has a length of 3¼ inches, the edge of the crimp is ⅛ of an inch long and the outside diameter of the opaque tube as shown in FIG. 3 is 3/8 of an inch.

EXAMPLE 2

CLINICAL TESTING

Clinical testing was conducted with 90 patient fecal samples over a 4–5 day period collected from private institutions, hospitals, and clinics in northern Indiana. All patients were placed on restricted diets two days prior to and during the test, and the protocol as stated in the HEMOCCULT ® package insert was strictly adhered to. A total of 90 OCCULT-ALERT ™ tests and 90 HEMOCCULT ® tests were performed, and results summarized in the following table. The HEMOCCULT ® test was performed in duplicate as per that product package insert.

TABLE A

| CLINICAL SPECIMEN # | OCCULT-ALERT ™ | HEMOCCULT ® #1 | HEMOCCULT ® #2 |
|---|---|---|---|
| 1 | + | + | − |
| 2 | − | − | − |
| 3 | − | − | − |
| 4 | + | + | − |
| 5 | + | + | − |
| 6 | − | − | − |
| 7 | − | − | − |
| 8 | − | − | − |
| 9 | − | − | − |
| 10 | + | + | + |
| 11 | − | − | − |
| 12 | − | − | − |
| 13 | − | − | − |
| 14 | − | − | − |
| 15 | − | − | − |
| 16 | − | − | − |
| 17 | − | − | − |
| 18 | − | − | − |
| 19 | + | + | − |
| 20 | − | − | − |
| 21 | − | − | − |
| 22 | − | − | − |
| 23 | − | − | − |
| 24 | + | − | − |
| 25 | − | − | − |
| 26 | − | + | − |
| 27 | − | − | − |

TABLE A-continued

| CLINICAL SPECIMEN # | OCCULT-ALERT ™ | HEMOC-CULT ® #1 | HEMOC-CULT ® #2 |
|---|---|---|---|
| 28 | − | − | − |
| 29 | − | − | − |
| 30 | − | − | − |
| 31 | − | − | − |
| 32 | + | + | + |
| 33 | − | − | − |
| 34 | − | − | − |
| 35 | − | − | − |
| 36 | − | − | − |
| 37 | − | − | − |
| 38 | − | − | − |
| 39 | − | − | − |
| 40 | − | − | − |
| 41 | + | + | + |
| 42 | − | − | − |
| 43 | − | − | − |
| 44 | − | − | − |
| 45 | − | − | − |
| 46 | − | − | − |
| 47 | − | − | − |
| 48 | + | + | − |
| 49 | − | − | − |
| 50 | − | − | − |
| 51 | − | − | − |
| 52 | − | − | − |
| 53 | − | − | − |
| 54 | − | − | − |
| 55 | − | − | − |
| 56 | − | − | − |
| 57 | − | − | − |
| 58 | − | − | − |
| 59 | − | − | − |
| 60 | − | − | − |
| 61 | − | − | − |
| 62 | − | − | − |
| 63 | − | − | − |
| 64 | − | − | − |
| 65 | − | − | − |
| 66 | − | − | − |
| 67 | − | − | − |
| 68 | − | − | − |
| 69 | − | − | − |
| 70 | − | − | − |
| 71 | − | − | − |
| 72 | − | − | − |
| 73 | − | − | − |
| 74 | − | − | − |
| 75 | − | − | − |
| 76 | − | − | − |
| 77 | − | − | − |
| 78 | + | + | + |
| 79 | − | − | − |
| 80 | − | − | − |
| 81 | − | − | − |
| 82 | − | − | − |
| 83 | − | − | − |
| 84 | − | − | − |
| 85 | − | − | − |
| 86 | + | + | + |
| 87 | − | − | − |
| 88 | − | − | − |
| 89 | − | − | − |
| 90 | − | − | − |

COMMENTARY ON CLINICAL TESTING

Samples were non-homogeneous and taken from different sections of the stool as per the HEMOCCULT ® protocol. Due to the non-homogeneity of the sample, some varience in test results were noted between HEMOCCULT ® #1 and HEMOCCULT ® #2. OCCULT-ALERT ™ gave identical results with HEMOCCULT ® test #1 in 88/90 (98%) of the clinical specimens. HEMOCCULT ® test #1 gave identical results with HEMOCCULT ® test #2 in 83/90 (92%) of the clinical specimens. OCCULT-ALERT ™ gave identical results with HEMOCCULT ® test #2 in 83/90 (92%) of the clinical specimens.

ADDITIONAL FECAL SAMPLES

Additional data was obtained with further fecal samples. Clinical specimens were obtained from patients placed on a restricted diet two days prior to the test. All samples tested negative for occult blood with HEMOCCULT ®. To these samples, known concentrations of commercially available hemoglobin was added and samples homogenized.

The following results were obtained:

| CONCENTRATION OF HEMOGLOBIN | SAMPLE NUMBER | OCCULT-ALERT ™ | HEMOCCULT ® #1 | HEMOCCULT ® #2 |
|---|---|---|---|---|
| 2 mg | 1 | − | | |
|  | 2 | − | Test | |
|  | 3 | + | not | |
|  | 4 | + | performed | |
|  | 5 | + | | |
| 3 mg | 1 | + | + | + |
|  | 2 | + | + | + |
|  | 3 | + | + | + |
|  | 4 | + | + | + |
|  | 5 | + | + | + |
|  | 6 | + | + | + |
| 4 mg | 1 | + | + | + |
|  | 2 | + | + | + |
|  | 3 | + | + | + |
|  | 4 | + | + | + |
|  | 5 | + | + | + |
|  | 6 | + | + | − |
| 5 mg | 1 | + | + | + |
|  | 2 | + | + | + |
|  | 3 | + | + | + |
|  | 4 | + | + | + |
|  | 5 | + | | |
|  | 6 | + | | |
|  | 7 | + | | |
|  | 8 | + | | |
|  | 9 | + | | |
|  | 10 | + | | |
|  | 11 | + | | |
|  | 12 | + | | |
|  | 13 | + | Test | |
|  | 14 | + | not | |
|  | 15 | + | Performed | |
|  | 16 | + | | |
|  | 17 | + | | |
|  | 18 | + | | |
|  | 19 | + | | |
|  | 20 | + | | |
|  | 21 | + | | |
|  | 22 | + | | |
|  | 23 | + | | |
|  | 24 | + | | |

EXAMPLE 3

COMPARATIVE TEST EFFECT OF CONCENTRATION

Equivalency data was also obtained in the laboratories of BetaMED. In order to better establish the minimum concentration of hemoglobin detectable by OCCULT-ALERT ™, the following studies were conducted.

Five solutions of commercially available hemoglobin were prepared in distilled water. Aliquots of these solutions were applied to each test in such a manner as to insure application of the appropriate concentration of hemoglobin. The following results were obtained:

| CONC. | SAM-PLE | READING AT 30 SECONDS | | | | READING AT 3 MINUTES | | |
|---|---|---|---|---|---|---|---|---|
| | | OCCULT-ALERT | HEMOCCULT #1 | HEMOCCULT #2 | COLOSCREEN | OCCULT-ALERT | HEMOCCULT #1 | COLOSCREEN |
| 2.0 mg | 1 | + | + | + | + | + | + | + |
| | 2 | + | + | + | + | + | + | + |
| | 3 | + | + | + | + | + | + | + |
| 2.5 mg | 1 | + | + | + | + | + | + | + |
| | 2 | + | + | + | + | + | + | + |
| | 3 | + | + | + | + | + | + | + |
| 3.0 mg | 1 | + | + | + | + | + | + | + |
| | 2 | + | + | + | + | + | + | + |
| | 3 | + | + | + | + | + | + | + |
| 3.5 mg | 1 | + | + | + | + | + | + | + |
| | 2 | + | + | + | + | + | + | + |
| | 3 | + | + | + | + | + | + | + |
| 4.0 mg | 1 | + | + | + | + | + | + | + |
| | 2 | + | + | + | + | + | + | + |
| | 3 | + | + | + | + | + | + | + |

EXAMPLE 4

DIFFERENCES BETWEEN HEMOGLOBIN AND HUMAN WHOLE BLOOD

The OCCULT-ALERT TM test reacted identically with HEMOCCULT ® and COLOSCREEN. The results, however, are not representative of the sensitivity levels found in the fecal samples that were prepared with hemoglobin added.

To determine if there exists a difference between commercially available hemoglobin and human whole blood, the following study was performed. Heparinized whole blood containing 13.2 g/dl of hemoglobin was obtained and non-fecal laboratory specimens were prepared with the following concentrations of hemoglobin, and the following results obtained.

EXAMPLE 5

LOWER LIMIT OF DETECTION

There appears to be a lower limit of detection at the 2 mg/g level. These results correspond to existing literature, (see H. J. Wells, Comparison of the sensitivity of two tests for fecal occult blood, Coloscreen and Hemoccult. Am. Assoc. Clin. Chem. 1980 Annual Meeting, Boston, July, 1980).

To determine the sensitivity of OCCULT-ALERT TM in fecal material, the following study was conducted:

Five stool samples were obtained from a clinical laboratory in Indianapolis. All patients had been placed on a restricted diet 2 days prior to the test and stool samples were found to be negative for occult blood

| CONC. | SAM-PLE | READING AT 30 SECONDS | | | | READING AT 3 MINUTES | | | |
|---|---|---|---|---|---|---|---|---|---|
| | | OCCULT-ALERT | HEMOCCULT #1 | HEMOCCULT #2 | COLOSCREEN | OCCULT-ALERT | HEMOCCULT #1 | HEMOCCULT #2 | COLOSCREEN |
| 0 mg | 1 | − | − | − | − | − | − | − | − |
| | 2 | − | − | − | − | − | − | − | − |
| | 3 | − | − | − | − | − | − | − | − |
| 2.0 mg | 1 | + | + | + | + | + | + | + | |
| | 2 | − | + | + | + | − | + | + | + |
| | 3 | + | + | + | − | + | + | + | − |
| 2.5 mg | 1 | + | + | + | + | + | + | + | + |
| | 2 | + | + | + | + | + | + | + | + |
| | 3 | + | + | + | + | + | + | + | + |
| 3.0 mg | 1 | + | + | + | + | + | + | + | + |
| | 2 | + | + | + | + | + | + | + | + |
| | 3 | + | + | + | + | + | + | + | + |
| 3.5 mg | 1 | + | + | + | + | + | + | + | + |
| | 2 | + | + | + | + | + | + | + | + |
| | 3 | + | + | + | + | + | + | + | + |
| 4.0 mg | 1 | + | + | + | + | + | + | + | + |
| | 2 | + | + | + | + | + | + | + | + |
| | 3 | + | + | + | + | + | + | + | + | using HEMOCCULT ® and COLOSCREEN.

Whole blood containing 13.2 g/dl hemoglobin was added to the samples in the following concentrations and homogenized.

| CONC. | SAM-PLE | READING AT 30 SECONDS | | | READING AT 3 MINUTES | | |
|---|---|---|---|---|---|---|---|
| | | OCCULT-ALERT | HEMOCCULT | COLORSCREEN | OCCULT-ALERT | HEMOCCULT | COLOSCREEN |
| 0 mg | 1 | − | − | − | − | − | − |
| | 2 | − | − | − | − | − | − |
| | 3 | − | − | − | − | − | − |
| | 4 | − | − | − | − | − | − |
| | 5 | − | − | − | − | − | − |

| CONC. | SAM-PLE | READING AT 30 SECONDS | | | READING AT 3 MINUTES | | |
|---|---|---|---|---|---|---|---|
| | | OCCULT-ALERT | HEMOCCULT | COLORSCREEN | OCCULT-ALERT | HEMOCCULT | COLORSCREEN |
| 1 mg | 1 | − | − | − | − | − | − |
| | 2 | − | − | − | − | − | − |
| | 3 | − | − | − | − | − | − |
| | 4 | − | − | − | − | − | − |
| | 5 | − | − | − | − | − | − |
| 2 mg | 1 | + | − | + | + | − | + |
| | 2 | − | − | − | − | − | − |
| | 3 | − | + | − | − | + | − |
| | 4 | + | + | + | + | + | + |
| | 5 | − | − | − | − | − | − |
| 2.5 mg | 1 | + | + | + | + | + | + |
| | 2 | − | − | − | − | − | − |
| | 3 | − | − | − | − | − | − |
| | 4 | − | − | − | − | − | − |
| | 5 | + | + | + | + | + | + |
| 3.0 mg | 1 | + | + | + | + | + | + |
| | 2 | − | − | − | − | − | − |
| | 3 | − | − | − | + | − | − |
| | 4 | + | + | + | + | + | + |
| | 5 | + | + | + | + | + | + |
| 3.5 mg | 1 | + | + | + | + | + | + |
| | 2 | − | − | − | − | − | − |
| | 3 | + | + | + | + | + | + |
| | 4 | − | − | − | − | − | − |
| | 5 | + | + | + | + | + | + |
| 4.0 mg | 1 | − | − | − | − | − | − |
| | 2 | + | + | + | + | + | + |
| | 3 | + | + | + | + | + | + |
| | 4 | + | + | + | + | + | + |
| | 5 | + | + | + | + | + | + |
| 6.0 mg | 1 | + | + | + | + | + | + |
| | 2 | + | + | + | + | + | + |
| | 3 | + | + | + | + | + | + |
| | 4 | + | + | + | + | + | + |
| | 5 | + | + | + | + | + | + |
| 8.0 mg | 1 | + | + | + | + | + | + |
| | 2 | + | + | + | + | + | + |
| | 3 | + | + | + | + | + | + |
| | 4 | + | + | + | + | + | + |
| | 5 | + | + | + | + | + | + |

From the results with laboratory prepared homogenized fecal samples the lower limit of detection was determined to be 2 mg/g. Consistent results were obtained at the 4 through 8 mg/g level. These findings correspond to published studies on homogenized samples. See H. J. Wells, Comparison of the sensitivity of two tests for fecal occult blood, Coloscreen and Hemoccult. Am. Assoc. Clin. Chem. 1980 Annual Meeting, Boston, July, 1980.

EXAMPLE 6
AGE OF SAMPLE

To ascertain the length of time the stool sample may remain on the cotton tip of the OCCULT-ALERT ™ test prior to development, the following study was conducted. A stool sample obtained from a patient on a restricted diet 2 days prior to testing was obtained and was prepared with whole blood at a concentration of 4 mg HB/g feces. The following results were obtained with duplicate tests.

| | Positive | | Control | |
|---|---|---|---|---|
| Day | Test 1 | Test 2 | Test 1 | Test 2 |
| 0 | + | + | − | − |
| 1 | + | + | − | − |
| 2 | + | + | − | − |
| 3 | + | + | − | − |
| 4 | + | + | − | − |
| 5 | + | + | − | − |
| 6 | + | + | − | − |
| 7 | + | + | − | − |
| 8 | + | + | − | − |
| 9 | + | + | − | − |
| 10 | + | + | − | − |
| 11 | + | + | − | − |
| 12 | + | + | − | − |

This data indicates that tests may remain undeveloped for 12 days which is more than sufficient time for the patient to return the test to the physician or laboratory. This also corresponds to the time period recommended for HEMOCCULT ® and COLOSCREEN.

In the foregoing examples the preferred formulation illustrated in the drawings for the manufacture of the chromogen pledget as shown in FIG. 6 and for the assembly of the device as shown in FIGS. 1 through 5 is based upon the selected optimum concentration of the chromogen TMB at a level of 0.40 grams of TMB and 0.40 grams of 6 MEQ dissolved in 50 milliliters of chromogen.

The material of the pledget which is the preferred material is a carded cotton of very light weight sold under the Trademark WEBRIL of a dimension of either 1/16 inch or 1/32 inch. The inventors have used other materials such as filter paper as an example of a bibulous material which can be used for dipping into the precoating solution of buffer and hydroxyethylcellulose before being impregnated by dipping into a chromogen solution in chloroform or alternatively a chromogen-stabilizing solution, TMB and 6 MEQ in chromogen. Each of the inventors have prepared test papers in this fashion by following the procedure of FIG. 6 to provide a pledget which will react with the sample of fecal matter containing occult blood in the presence of hydrogen peroxide. However, bibulous material such as paper, flexible cardboard, or wood or the like are not preferred because they stiffen due to the amount of material which is imbibed and taken up in the impregnation steps involved in the coatings consisting of the first pre-coating, a coating with buffer and hydroxyethylcellulose in water and sodium decyl sulphate followed by drying and a second impregnation from organic solvent. The handling characteristics of the chromogen are totally different from those of the chromogen used in applicant's prior patents, e.g. from para phenylene diamine dihydrochloride salt. The salt used in the prior patents is relatively unstable, yet readily dissolved in water and its purity must be monitored precisely. The chromogen for this other test is color sensitive and relatively unstable to heat and to long time storage unless extraordinary efforts are maintained to maintain the purity to the highest possible level.

In contrast, TMB as a base has no affinity for water and does not dissolve in a 95% ethyl alcohol. It can not be put into solvent containing water such as ethyl alcohol. However, when impregnation is carried out in accordance with FIG. 6, using organic solvent such as chloroform, positive color change could be observed for the TMB whether in a paper pledget or a cotton web pledget within 1 to 2 seconds and never beyond 5 seconds.

It was possible, where the amount of the reagent was cut down from 0.4 grams of TMB to less than 0.1 gram and the impregnated web squeezed to get rid of all excess material to observe much weaker color changes.

Experiments were tried to determine the effect of the buffers on the testing procedure and the storage stability of the testing device. It was quickly discovered that volatile buffers such as those containing hydrochloric acid were unsatisfactory because of variation of pH which resulted unless a very careful control as by electrometric titration was instituted in order to provide the proper pH. The results discovered that less water-soluble buffers were not useful, and in particular the phosphate buffers which tend to react with alkaline earth materials such as calcium or magnesium are less preferred than the organic acids.

Other dispersing agents comparable in function to sodium decyl sulfate could be used and these are well known in the art. However, sodium decyl sulfate is a well recognized reagent in biochemistry analysis. Its characteristics are well recognized, its limitations are well known, and its safety characteristics are equally well recognized and appreciated. The keeping qualities of the chromogen pledget and the device is best upon utilization of simple pure reagents and the avoidance of compositions such as gelatin and agar and gums such as gum arabic which are known excipients for tabletting and the like are not contemplated as ingredients of the solutions used for impregnation.

It is possible to prepare less concentrated solutions of the chromogen in solvents other than alcohol but the concentration of the chromogen is so reduced and the color effect so diminished that a serious question of the reliability of the test comes into question if one departs from the simple two-dip two-coat procedure of FIG. 6.

What is claimed is:

1. A self-contained swab cartridge apparatus for detection of occult blood in a fecal sample comprising:
   a tubular flexible cartridge having a closed end and an open end;
   A swab protruding from the open end of said cartridge for holding a sample of fecal matter;
   a cap having an open end and a closed end and adapted to close said cartridge and cover said swab;
   a chromogen-pledget positioned in said cap comprising a web of fibrous absorbent material that has been impregnated first with a precoating of an aqueous solution of hydroxyethylcellulose and a non-volatile acid buffer capable of providing a pH of between 5 and 7 during use and then further impregnated with a volatile solvent solution of 3,3',5,5'-tetramethylbenzidine and 6-methoxyquinoline;
   an ampoule positioned in said cartridge between its closed end and the swab, said ampoule being made of frangible material and filled with a unit dosage of about 0.75–1 ml of a dilute aqueous hydrogen peroxide solution containing a wetting agent in an amount sufficient to assure complete solubilization of the hydroxyethylcellulose;
   whereby when the ampoule is broken, the dilute aqueous hydrogen peroxide solution containing the wetting agent transports a sample to the chromogen-pledget in the cap and solubilizes said hydroxyethylcellulose along with the buffer, 3,3',5,5'-tetramethylbenzidine, and 6-methoxyquinoline to form an aqueous color development medium having a pH of between 5 and 7 and develop, in 1–2 seconds in the presence of any occult blood in the sample, a vivid green color that lasts 8 months or longer.

2. A swab apparatus as claimed in claim 1 wherein said chromogen-pledget is of a size so that it touches the end of the swab when the cap closes the cartridge and covers the swab.

3. A swab apparatus as claimed in claim 1 wherein the hydrogen peroxide in said dilute aqueous hydrogen peroxide solution is present in a concentration of 3% by weight.

4. A swab apparatus as claimed in claim 3 wherein said wetting agent is sodium decyl sulfate in a concentration of from 0.5% to 1% by weight.

5. A swab apparatus as claimed in claim 3 wherein the volatile solvent solution comprises a 100 ml chloroform solution containing 0.4 grams of 3,3',5,5'-tetramethylbenzidine and 0.4 grams of 6-methoxyquinoline.

6. A swab apparatus as claimed in claim 5, wherein buffer comprises a mixture of citric acid and sodium citrate.

7. A swab apparatus as claimed in claim 5 wherein said chromogen-pledget is formed of cotton and dried after each impregnation.

* * * * *